US006228995B1

(12) United States Patent
Lee

(10) Patent No.: US 6,228,995 B1
(45) Date of Patent: *May 8, 2001

(54) METHOD FOR REMOVAL OF PSORALENS FROM BIOLOGICAL FLUIDS

(75) Inventor: Kyu H. Lee, Bryn Mawr, PA (US)

(73) Assignee: Therakos, Inc., Exton, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/835,777

(22) Filed: Apr. 8, 1997

Related U.S. Application Data

(60) Provisional application No. 60/015,071, filed on Apr. 9, 1996.

(51) Int. Cl.[7] .............................. A23J 1/00; C07K 1/00; C07K 14/00; C07K 16/00
(52) U.S. Cl. ........................ 530/412; 530/413; 530/415; 435/2; 210/669; 210/694
(58) Field of Search ............................. 530/412, 413, 530/415; 435/2; 210/669, 694

(56) References Cited

U.S. PATENT DOCUMENTS

| D. 298,279 | 10/1988 | Lee et al. . |
| D. 298,567 | 11/1988 | Morris . |
| D. 299,531 | 1/1989 | Troutner et al. . |
| D. 299,953 | 2/1989 | King et al. . |
| 4,196,281 | 4/1980 | Hearst et al. . |
| 4,321,919 | 3/1982 | Edelson . |
| 4,398,906 | 8/1983 | Edelson . |
| 4,428,744 | 1/1984 | Edelson . |
| 4,452,811 | 6/1984 | della Ville . |
| 4,464,166 | 8/1984 | Edelson . |
| 4,464,354 | 8/1984 | Bisagni et al. . |
| 4,465,691 | 8/1984 | Bisagni et al. . |
| 4,568,328 | 2/1986 | King . |
| 4,573,960 | 3/1986 | Goss . |
| 4,573,961 | 3/1986 | King . |
| 4,573,962 | 3/1986 | Troutner . |
| 4,578,056 | 3/1986 | King et al. . |
| 4,596,547 | 6/1986 | Troutner . |
| 4,612,007 | 9/1986 | Edelson . |
| 4,613,322 | 9/1986 | Edelson . |
| 4,623,328 | 11/1986 | Hartranft . |
| 4,643,710 | 2/1987 | Troutner . |
| 4,681,568 | 7/1987 | Troutner . |
| 4,683,889 | 8/1987 | Edelson . |
| 4,684,521 | 8/1987 | Wdelson . |
| 4,687,464 | 8/1987 | Troutner . |
| 4,692,138 | 9/1987 | Troutner et al. . |
| 4,693,981 | 9/1987 | Wiesehahn et al. . |
| 4,705,498 | 11/1987 | Goss . |
| 4,708,715 | 11/1987 | Troutner et al. . |
| 4,726,949 | 2/1988 | Miripol et al. . |
| 4,727,027 | 2/1988 | Wiesehahn et al. . |
| 4,737,140 | 4/1988 | Lee et al. . |
| 4,748,120 | 5/1988 | Wiesehahn et al. . |
| 4,838,852 | 6/1989 | Edelson et al. . |
| 4,866,282 | 9/1989 | Miripol et al. . |
| 4,897,789 | 1/1990 | King et al. . |
| 4,921,473 | 5/1990 | Lee et al. . |
| 4,952,812 | 8/1990 | Miripol et al. . |
| 4,960,408 | 10/1990 | Klainer et al. . |
| 4,999,375 | 3/1991 | Bachynsky et al. . |
| 5,030,200 | 7/1991 | Judy et al. . |
| 5,176,921 | 1/1993 | Wiesehahn et al. . |
| 5,216,176 | 6/1993 | Heindel et al. . |
| 5,288,605 | 2/1994 | Lin et al. . |
| 5,356,929 | 10/1994 | Heindel et al. . |
| 5,360,734 | 11/1994 | Cgaonab et al. . |
| 5,459,030 | 10/1995 | Lin et al. . |
| 5,482,828 | 1/1996 | Lin et al. . |
| 5,651,993 | 7/1997 | Edelson et al. . |
| 5,660,731 | * 8/1997 | Piechocki et al. .................... 210/669 |
| 5,709,991 | * 1/1998 | Lin et al. ................................ 435/2 |

FOREIGN PATENT DOCUMENTS

| 88302660 | 3/1988 | (EP) . |
| 62283190 | * 12/1987 | (JP) . |
| WO93/14791 | 1/1993 | (WO) . |
| WO95/03814 | 7/1994 | (WO) . |

OTHER PUBLICATIONS

Freifelder: Physical Biochemistry Applications to biochem. and Mol. Bio. 2nd. Ed. :pp. 238–257, 1982.*

Richard Edelson et al. "Treatment of Cutaneous T–cell Lymphoma By Extracorporeal Photochemotherapy" New England Journal of Medicine 316:297–303 (Feb. 5, 1987).

Marglis–Nunno et al."Elimination of Potential Mutagenicity in Plantelet Concentrates that are virally Inactivate with Psoralens and Ultraviolet A Light" Transformation 1985:pp. 855–862.

Hoofnagle et al. Treatment of chronic Non–A, Non–B Hepatitis with Recombinant Human Alpha interferon New England Journal of Medicine vol. 315 No. 25 pp. 1575–1578.

Davis et al. "Treatment of Chronic Hepatitis C with Recombinant Interferon Alfa" New England Journal of Medicine vol. 321 No. 22 pp. 1501–1505.

De Bisceglie et al. "Recombinant Interferon Alfa Therapy for Chronic Hepatitis C" New England Journal of Medicine vol. 321 No. 22 pp. 1506–1510.

Farci et al "A Long–term Study of Hepitatis C Virus Replication in non–A, Non–B Hepatitis" New England Journal of Medicine vol. 325 No. 2 pp. 98–103.

(List continued on next page.)

Primary Examiner—Jeffrey Stucker
Assistant Examiner—Brett Nelson

(57) ABSTRACT

A method for the removal of psoralens and psoralen degradation products is disclosed. The method of the present invention is useful for any biological fluid that has been treated with psoralens, including blood and blood fractions and components derived therefrom. Biological fluids treated according to the method of the present invention are substantially free from any residual psoralens or psoralen degradation products.

7 Claims, 3 Drawing Sheets

OTHER PUBLICATIONS

Shindo et al. "Decrease in Serum Hepatitis C Viral RNA during Alpha–Interferon Therapy for Chronic Hepatitis C" Annals of Internal Medicine vol. 115 No. 9 pp. 701–704.

"High Dose Interferon Alfa–2A for the Treatment of Chronic Hepatitis C" The Annals of Pharmacotherpy 1994 Mar. vol. 28 pp. 341–342.

M. Gomez–Rubio et al. "Prolonged Treatment (18 months) of Chronic Hepatitis C with Recombinant α–Interferon in comparison with a control group" Journal of Hepatology, 1990:11:S63–S67.

Saez–Royuela et al. "High Doses of Recombinant α–Interferon or γ–Interferon from Chronic Hepatitis C: A Randomized, Controlled Trial" Hepatology 1991; 13:No. 2 327–331.

Nakano et al. "Comparative Study of Clinical, Histological, and Immunologics Responses to Interferon Therapy in Type Non–A, Non–B, and Type B Chronic Hepatitis" The American Journal of Gastroenterology vol. 85; No. 1.1990.

Haysahi et al. "Improvement of Serum Aminotransferase Levels after Phlebotomy in Patients with chronic Active Hepatitis C and Excess Hepatic Iron" The American Journal of Gastroenterology vol. 89; No. 7.1994 pp. 986–988.

Ljunggren et al. "Plasma Levels of 8 Methoxypsoralen Determined by High–Pressure Liquid Chromatography in Psoriatic Patients Ingesting Drug from Two Manufacturers" The Journal of Investigative Dermatology, vol. 74, No. 1 pp. 59–62.

Christer T. Jansen et al. "Inter–and Intraindividual Variations in Serum Methoxsalen Levels During Repeated Oral Exposure" Therapeutic Research vol. 33, No. 2 pp. 258–264.

Michael J. Clemens et al. "Regulation of Cell Proliferation and Differentation by Interferons" Brochena J. (1985) 226, 345–360.

Witter et al. "Efffects of Prednisone, Aspirin, and Acetaminophen on an in vivo biologic response to interferon in humans" Clin Pharmacol Ther Aug. 1988 pp. 239–243.

Alain H. Rook, et al. "Combined Therapy for Sezary Syndrome With Extracorporeal Photochemotherapy and Low Dose Interferon Alfa Therapy" Arch Dermatol. 1991;127: pp. 1535–1540.

Alain H. Rook, et al. "Treatment of Autoimmune Disease with Extracorporeal Photochemotherapy: Pemphigus Vulgaris" The Yale Journal of Biology and Medicine 62 (1989). 647–652.

Barr et al. "Immunomodulation with photopheresis: Clinical Results of the Multi–Center Cardiac Transplantation Study" Study supported by THERAKOS, A Johnson & Johnson Company.

Costanzo–Nordin et al. "Successful Treatment of Heart Transplant Rejection with Photopheresis" Transplantation vol. 53, 808–815, No. 4 Apr. 1992.

Meiser et al. Reduction of the Incidence of rejection by Adjunct Immunosuppression with Photochemotherapy After Heart Transplantation Transplantation vol. 57 563–566 No. 4 Feb. 1994.

Vowels et al. "Extracorporeal Photochemotherapy Induces the Production of Tumor Necrosis Factor–α by Monocytes: Implications for the Treatment of Cutaneous T–ell Lymphoma and Systemic Scelerosis" The Journal of Investigative Dermatology, Inc. vol. 98:686–692,1992.

Gil et al. Hepatic and Extrahepatic HCV RNA Strands in Chronic Hepatitis C: Different Patterns of Respons to Interferon Treatment Hepatology 1993; 18, 1050–1054.

Qian et al. "Replication of hepatitis C Virus in peripheral blood mononuclear cells" Journal of Hepatology 1992;16:380–383.

Elcanor C. Mandoza et al. "Decreased Phorbol Myristate Acetate–Induced Release of Tumor Necrosis Factor–α and Interleukin–1β from Peripheral Blood Monocytes of Patients Chronically Infected with Hepatitis C Virus" Journal of Infectious Disease 1996 vol. 174 pp. 42–44.

Zignego et al. "Infection of peripheral mononuclear blood cells by hepatitis C Virus" Journal of Hepathology, 1992;15:382–386.

Mutsunori Shirai et al. "Introduction of Cytotoxic T Cells to a Cross–Reactive Epitope in the Hepatitis C. Virus Nonstructural RNA polymerase–Like Protein" Journal of Virology, Jul. 1992;pp. 4098–4106.

Kanei et al. "Supression of hepatitis C virus RNA by interferon–λ." The Lancet vol. 336 p. 245.

Amy J. Weiner et al. "Evidence for immune selection of hepatitis C virus (HCV) putative enveolpe glycoprotein variants: Potential role in chronic HCV infections" Proc. Natl. Acad. Sci. USA vol. 89 pgs. 3468–3472.

Shimizu et al. "Early events in hepatitis C. Virus infection of chimpanzees" Proc. Natl. Acad. Sci. USA 87 pp. 6441–6444.

J. A. Garson et al. "Enhanced detection by PCR of hepatitis C virus RNA" The Lancet Oct. 6, 1990 p. 878.

P. Simmonds et al. "Classification of hepatitis C virus into six major genotypes and a series of subtypes by phylogenetic analysis of the NS–5 region" Journal of General Virology (1993). 74 2391–2399.

Houghton et al. "Monecular Biology of the Hepatitis C Virues: Implications for Diagnosis, Development and Control of Viral Disease" Hepatology vol. 14, No. 2 1991 pp. 381–388.

Choo et al. "Genetic organization and diversity of the hepatitis C virus" Proc. Natl. Acad. Sci. USA vol. 88, pp. 2451–2455.

Choo et al. "Isolation of a cDNA Clone Derived from a Blood Bone Non–A, Non–B Viral Hepatitis Genome".

Ronald L. Koretz et al. "Non–A, Non–B Posttransfusion Hepatitis A Decade Later" Gastroenterology 1985:88:1251–4.

Jules L. Dienstag Non–A, Non–B Hepatitis, I. Recognition, Epidemiology, and Clinical Features Gastroenterology vol. 85. No. 2.

Flavio Rossetti, et al. "Extracorporeal Photochemotherapy as single therapy for extensive, Cutaneous, Chronic Graft–versus–Host Disease" Transplantation vol. 59 No. 1 pp. 150–151.

"American Liver Foundation" Progress, 1994–95, vol. 16, pp. 1–12.

Alain H. Rook, MD et al. "Treatment of Systemic Sclerosis With Extracorporeal Photochemotherapy" Archives of Dermatology 1992;128:337–346.

Malawista et al. "Treatment of Rheumatoid Arthritis by Extracorporeal Photochemotherapy" Arthritis and Rheumatism, vol. 34, No. 6 pp. 646–654.

Richard Edelson et al. "Treatment of Cutaneous T–Cell Lymphoma by Extracorporeal Photochemotherapy" New England Journal of Medicine 316:297–304.

Richard Edelson et al. "Photopheresis: a Clinocally Relevant Immunobiologic Response Modifier"Dept. of Dermatology Yale Univ. School of Medicine.

Grass et al. "Inactivation of Leukocytes in Platelet Concentrates by Photochemical Treatment with Psoralen Plus UVA" The American Society of Hematology. Blood, vol. 91, No. 6 pp. 2180–2188.

* cited by examiner

METHOD FOR REMOVAL OF PSORALENS FROM BIOLOGICAL FLUIDS

This application claims benefit of provisional patent application No. 60/015,071 filed Apr. 9, 1996.

BACKGROUND OF THE INVENTION

Recently, because of potential risks involved with donated blood, methods for inactivating pathogenic agents that may be found in donor blood or blood components are being actively investigated. One of the most promising approaches is inactivating pathogenic agents by photochemical treatment. One of the main problems in most photochemical treatment methods is reducing the residual photosensitizer or its decomposed products in the treated blood to sufficiently low level so that the treated blood or blood product can be transfused to patients. Even though all donor blood is tested for possible contamination with known pathogens it is currently not possible to completely eliminate all contaminated blood from the donor blood pool.

This is caused by several circumstances. For instance, when a person is infected with viruses such as human immunodeficiency viruses (HIV) which causes AIDS, there is a period during which the anti-HIV antibody titer is too low for positive detection by current screening tests. Therefore, blood donated by an HIV infected person during this period may pass the antibody screening tests and could infect any recipients of the donated blood or blood products made therefrom. Also, there is always the possibility that the donated blood is contaminated by unknown or undetected pathogens. For these reasons currently there is an urgent need for methods to eliminate those undetected pathogens in the donated blood or blood components derived therefrom for human use.

Wiesehahn et al. (U.S. Pat. Nos. 4,727,027; 4,748,120; and 5,176,921) and Isaacs et al. (U.S. Pat. No. 5,139,940) described methods for deactivating pathogens in biological fluids by UVA irradiation in the presence of psoralen derivatives such as 8-methoxy psoralen(8-MOP), 4'hydroxymethyl-4,5',8-trimethylpsoralen (HMT), 4'-aminomethyl-4',5'8-trimethylpsoralen(AMT), or other psoralen derivatives. In this process only a small fraction of the total amount of psoralen compound added is consumed in inactivating those pathogens and the remainder of the added psoralen compound either remains in the treated blood as original psoralen compound or remains in the treated blood as psoralen decomposition products.

The amount of these residual compounds in the treated blood or blood component could be very substantial and when a patient is transfused with this treated blood or blood component the patient may be exposed to psoralens or psoralen degradation products. This exposure to psoralens or psoralen degradation products may in turn cause undesirable effects on the patient such as phototoxicity or other toxic effects associated with psoralen and their decomposition products. Therefore, it is highly desirable to remove the remaining psoralen derivatives or decomposed psoralen products from the treated blood or blood component before any human use.

Currently there are no methods published which have been shown to remove the psoralen compounds and their decomposition products from blood and blood products.

SUMMARY OF THE INVENTION

The present invention is drawn to a method for the removal of psoralen compounds and their decomposition products from psoralen-treated biological fluids, including but not limited to, blood and blood products. The method of the present invention utilizes a psoralen-adsorbent material which is contacted with the psoralen-treated biological fluid, such as blood or blood products. Biological fluids, blood or blood products that contain psoralen compounds or their decomposition products are treated according to the method of the present invention to produce a biological fluid, blood and blood components that are substantially free from psoralen compounds or psoralen decomposition products.

DETAILED DESCRIPTION OF THE INVENTION

Figure 1:
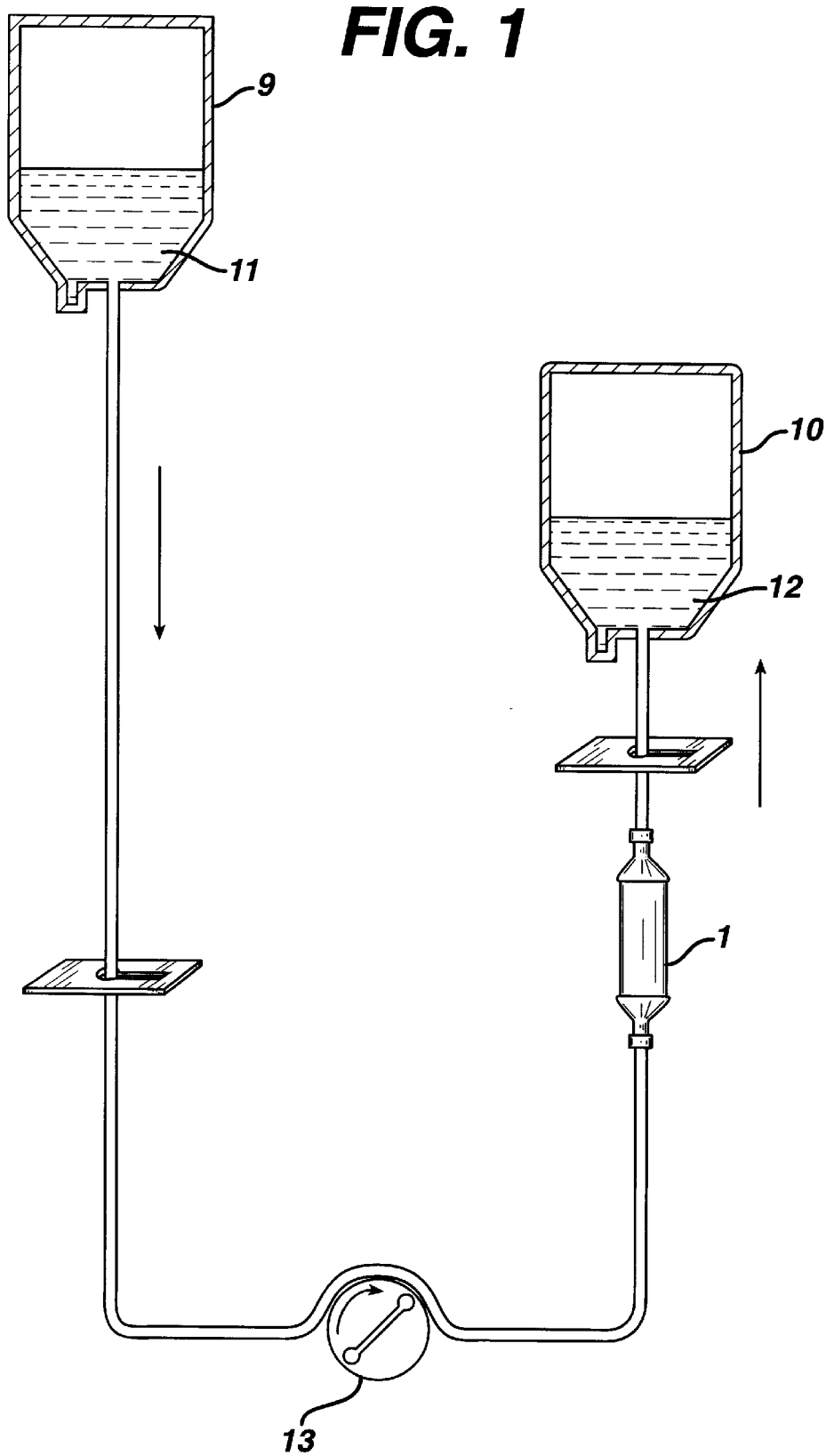
FIG. 1 shows an overall general view of the usage of this adsorption device. The first container(9) contains already irradiated blood or blood component(11) which contains residual psoralen or psoralen derivatives such as 8-MOP, AMT, HMT or other psoralen derivative and its decomposition products during earlier ultraviolet A irradiation. The treated fluid(11) is pumped by the pump(13) through the adsorption device(1), where the residual photosensitizer(s) or its byproducts are removed, into the second container(10).
Figure 2:
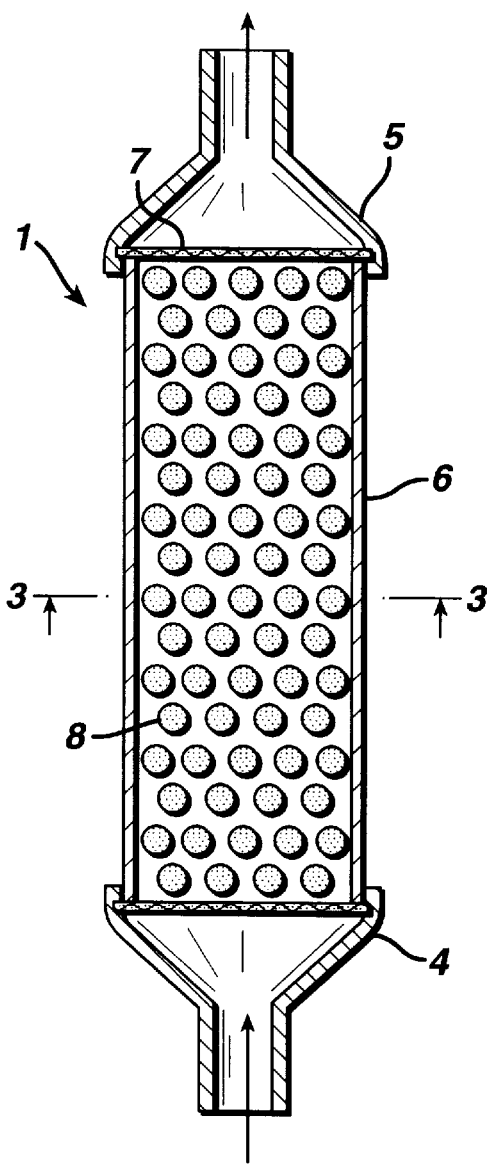
FIG. 2 shows a vertical cross-sectional view of the adsorption device(1). The cartridge is made of inlet cap(4), outlet cap(5), body casing(6), two stainless steel screens(7), and adsorbent(8). The stainless screens(7) contain the resin beads inside the cartridge and prevent them from coming out of the cartridge.
Figure 3:
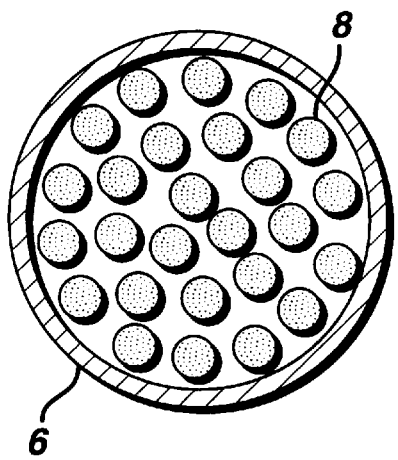
FIG. 3 shows a horizontal cross-sectional view of the device(1). The adsorbent(8) is microporous beads of the size approximately 0.1–2mm in diameter and made from polystyrene or polystyrene copolymerized with divinylbenzene. These microporous beads have pore sizes in the range of molecular level, 10–1000 Angstroms, and large pore surface area, 100–1,000 square meter per gram of the adsorbent. Good examples are XAD-4 and XAD-16 resin beads made by Rohm and Haas Company.
Figure 4:
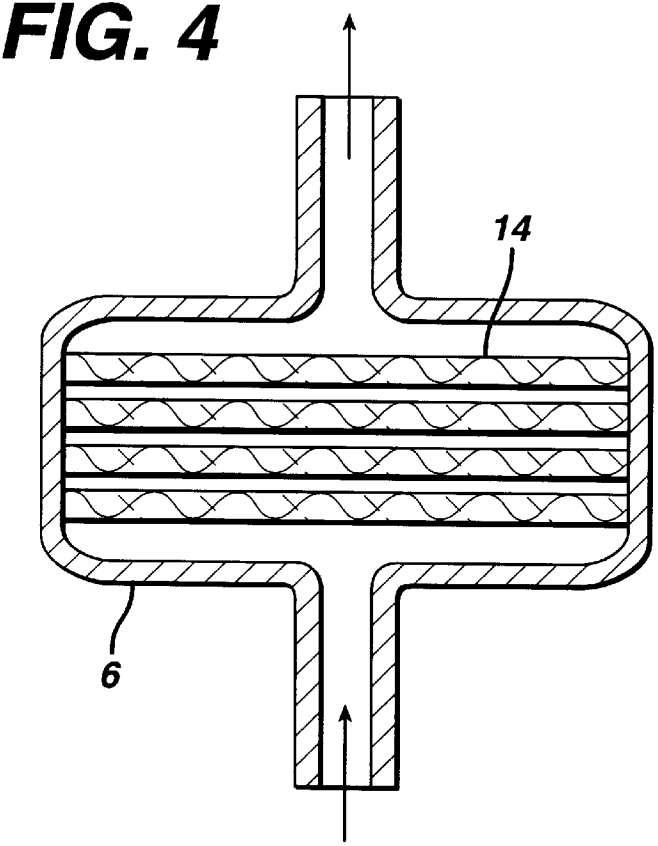
FIG. 4 shows a cross-sectional view of another design of this invention. Here the adsorbent(14) is made of microporous fibers(14) instead of beads. The fibers could be in woven or non-woven configuration. By using fibers instead of beads the stainless steel screens(7) can be eliminated.
Figure 5:
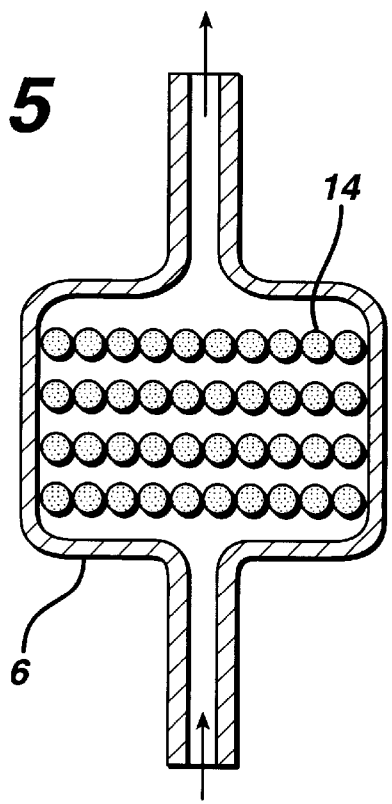
FIG. 5 shows a cross-sectional view of the same device shown in FIG. 4. Here the cross-sections of the adsorbent fibers are shown. These adsorbent fibers are woven with other fine threads.

It is the purpose of this invention to develop a method to remove the residual photosensitizers such as psoralen or its derivative(s) and its decomposition products, if any, from biological fluids such as treated blood or blood components so that the treated biological fluids can be transfused into patients substantially free from residual photosensitizer(s). Biological fluids that are suitable for use in the method of the present invention include, but are not limited to, whole blood, serum, plasma, blood fractions such as platelets, red cells, and buffy coat, extracts of blood or blood fractions such as proteins purified therefrom, and any biological fluid that has been treated with one or more psoralen compound.

Many psoralen adsorbent materials are suitable for use in the method of the present invention, and different physical forms of these materials can be made and are suitable for use in the method of the present invention. For instance, activated carbon in the form of microporous beads or fibers is a good psoralen adsorbent. But it has been found that activated carbon may also adsorb other components from blood or blood products. Therefore, its application in the method of the present invention is suitable only if the activated charcoal does not also remove a desirable component of the treated biological fluid. The preferred adsorbent materials for use in the method of the present invention are ones which adsorb the psoralens and psoralen decomposition products with minimum adsorption capacity for other desired components such as the components of blood and blood products for human use.

Microporous polymeric beads such as those made from polystyrene and polystyrene copolymerized with divinylbenzene are the preferred adsorbent materials for use in the method of the present invention for psoralen, psoralen derivatives and their photodecomposition products.

It is readily apparent to those of ordinary skill in the art that virtually any fluid is suitable for use in the method of the present invention. In particular, any biological fluids that have been treated with psoralen compounds are suitable for use in this method of the present invention. Biological fluids that are commonly exposed to psoralen compounds include, but are not limited to, whole blood, plasma, serum, and any components isolated from blood or blood fractions. Psoralen compounds have been used for a variety of purposes which include the sterilization of human blood and blood-derived products to prevent transmission of hepatitis viruses, herpes viruses, HIV and any other infectious or oncogenic entity derived from blood donors; the sterilization of cell culture-derived biologicals, such as interferons, enzymes, hormones and vaccines, to inactivate any viral or nucleic acid contaminants; and therapeutically in humans by treating patients with psoralens, and then irradiating the blood in an extracorporeal circuit, followed by the return of the psoralen-treated blood to the patient.

It is also readily apparent to one of ordinary skill in the art that a variety of different psoralen-adsorbent materials are suitable for use in the method of the present invention. Examples of suitable types of psoralen-adsorbent materials include, but are not limited to, activated carbon beads or fibers which are uncoated or coated with biocompatible materials, ion exchange resins such as DOWEX brand resin beads (commercially available from Dow Chemical Company, Midland Mich.), and AMBERLITE brand resin beads (commercially available from Rohm and Haas Company, Philadelphia, Pa.), with polystyrene and polystyrene copolymerized with divinylbenzene being most preferred.

It is readily apparent to those skilled in the art that the psoralen-treated biological fluid is contacted with the psoralen-adsorbent material in a variety of ways. For example, the biological fluid may be mixed in a batchwise fashion with the psoralen-adsorbent material, followed by removal of the psoralen-adsorbent material by standard separation means such as filtration or gravitational separation. Alternatively the psoralen-adsorbent material may be placed inside a standard chromatographic device such as a column through which is passed the psoralen-containing biological fluid.

It is also readily apparent to those skilled in the art that virtually any psoralen compound that is suitable for use in biological fluids, is suitable for use with the method of the present invention. Psoralen compounds are well known in the art and are described in U.S. Pat. No. 4,321,919; and U.S. Pat. No. 4,960,408. Commonly used psoralen compounds include, but are not limited to, psoralen; 8-methoxypsoralen; 4,5'8-trimethylpsoralen; 5-methoxypsoralen; 4-5'dimethyl-psoralen; 4,8-methylpsoralen; 4-methylpsoralen; 4,4-dimethylpsoralen; 4'-hydroxymethyl-4,5',8-trimethylpsoralen; and 4'-aminomethyl-4,5',8-trimethylpsoralen.

The following Examples are provided to illustrate the present invention without, however, limiting the same thereto.

EXAMPLE 1

In this experiment to demonstrate the adsorption capacity of styrene or styrene copolymer beads for psoralen derivatives, a glass pipette was used as a resin container and glass wool was used in place of stainless steel screen to keep the beads inside the pipette. A total of 8 grams of XAD-4 resin beads (commercially available from Rohm and Haas Co.) was filled into a pipette. Balls of glass wool were put at the bottom and top of the resin bed inside the pipette. The total bed volume of the resin beads was 11.4 mL. Several gallons of 0.5 ug/mL AMT (psoralen) solution in water was made, pumped through this small XAD-4 resin column, and AMT concentrations in the effluent was measured over time. The results are shown in Table 1.

TABLE 1

AMT Adsorption on XAD-4 Resin Column

| Run No. | Perfusion Rate mL/min. | Percent Leakage In Last Sample | Total Volume Treated-mL |
| --- | --- | --- | --- |
| 1 | 19.5 | 2.4 | 800 |
| 2 | 5.7 | 0.0 | 1,370 |
| 3 | 10.2 | 0.0 | 1,230 |
| 4 | 21.1 | 7.4 | 1,254 |
| 5 | 35.5 | 0.0 | 1,414 |
| 6 | 50.1 | 4.1 | 980 |
| | | total | 7,048 |

The test was carried out at six different flow rates with the same cartridge. As the flow rate increases the resident time of the perfusate in the resin cartridge decreases allowing less time for adsorption to take place. Therefore, if the adsorption rate is slow or the capacity is low, the AMT concentration in the effluent should increase. The test results show that the AMT concentration in the effluent is practically zero and not effected by flow rate increase. These results show that XAD-4 resin beads have extremely high affinity for AMT both in capacity and adsorption rate.

What is claimed is:

1. A method for the removal of psoralen compounds and psorlen degradation products from blood or blood products consisting essentially of:

a) contacting blood or blood products containing psoralen or psoralen degradation products with psoralen absorbent beads or fibers, provided that said psoralen absorbent beads or fibers are selected from the group consisting of ion exchange resins, polystyrene and polystyrene copolymerized with divinylbenzene to wherein the beads or fibers are in an amount sufficient to remove greater than ninety percent of the psoralen or psoralen degradation products to provide treated blood or blood products that can be transfused to a patient; and b) collecting the treated blood or blood products.

2. The method of claim 1 wherein the blood or blood products is serum.

3. The method of claim 1 wherein the blood or blood products is plasma.

4. The method of claim 1 wherein the blood or blood products is red blood cells.

5. The method of claim 1 wherein the blood or blood products is whole blood.

6. The method of claim 1 wherein the psoralen absorbent beads or fibers is selected from the group of polystyrene and polystyrene divinylbenzene copolymer.

7. The method of claim 1 wherein the psoralen is 8-methoxypsoralen.

* * * * *